US009939626B2

United States Patent
Rho et al.

(10) Patent No.: US 9,939,626 B2
(45) Date of Patent: Apr. 10, 2018

(54) MICROSCOPIC APPARATUS FOR CREATING SUPER-RESOLUTION IMAGES OF AN ORGANISM OR BIOLOGICAL MATTER AND METHOD FOR CREATING SUPER-RESOLUTION IMAGES OF AN ORGANISM OR BIOLOGICAL MATTER USING THE SAME

(71) Applicant: POSTECH Academy-Industry Foundation, Pohang-si (KR)

(72) Inventors: Junsuk Rho, Pohang-si (KR); Minkyung Kim, Pusan (KR)

(73) Assignee: POSTECH Academy-Industry Foundation, Pohang-si (KR)

( * ) Notice: Subject to any disclaimer, the term of this patent is extended or adjusted under 35 U.S.C. 154(b) by 24 days.

(21) Appl. No.: 15/077,377

(22) Filed: Mar. 22, 2016

(65) Prior Publication Data

US 2016/0306157 A1    Oct. 20, 2016

(30) Foreign Application Priority Data

Apr. 16, 2015   (KR) .................. 10-2015-0053700

(51) Int. Cl.
  *G02B 21/00* (2006.01)
  *G02B 21/36* (2006.01)
  (Continued)

(52) U.S. Cl.
  CPC ....... *G02B 21/361* (2013.01); *G01N 33/4833* (2013.01); *G02B 27/56* (2013.01); *G02B 27/58* (2013.01); *G02B 1/002* (2013.01)

(58) Field of Classification Search
  CPC .......... G02B 1/00; G02B 1/002; G02B 1/005; G02B 1/007; G02B 21/00; G02B 21/06; G02B 21/08; G02B 21/082; G02B 21/34
  (Continued)

(56) References Cited

U.S. PATENT DOCUMENTS

| 8,213,089 B2 | 7/2012 | Lee et al. |
| 8,879,158 B2 | 11/2014 | Choi et al. |
| 2010/0134898 A1* | 6/2010 | Shalaev ................. B82Y 20/00 359/665 |

FOREIGN PATENT DOCUMENTS

| JP | 2008083704 | 4/2008 |
| JP | 2011227422 | 11/2011 |
| KR | 10-2011-0060404 | 6/2011 |
| KR | 101075030 | 10/2011 |

(Continued)

OTHER PUBLICATIONS

Z. Liu, H. Lee, Y. Xiong, C. Sun, X. Zhang, 'Far-field optical hyperlens magnifying sub-diffraction-limited objects', Science, vol. 315, Mar. 23, 2007, pp. 1686.*

*Primary Examiner* — Arnel C Lavarias
(74) *Attorney, Agent, or Firm* — H.C. Park & Associates, PLC (57) ABSTRACT

An optical microscopic apparatus for creating a super-resolution image of an organism or biological matter, the optical microscopic apparatus includes a light source configured to provide visible light including evanescent waves, a hyper-lens unit including a front surface on which a specimen is placed, the hyper-lens unit including a multi-layered structure to convert at least part of the evanescent waves incident on the front surface into propagating waves, an objective lens for collecting visible light emitted from a rear surface of the hyper-lens unit, and an image capturing unit to capture visible light emitted from the objective lens and to create an image of the specimen.

19 Claims, 6 Drawing Sheets

(51) Int. Cl.
*G02B 27/56* (2006.01)
*G02B 27/58* (2006.01)
*G01N 33/483* (2006.01)
*G02B 1/00* (2006.01)

(58) Field of Classification Search
USPC ....... 359/362, 363, 364, 368, 369, 385, 386, 359/387, 388, 389, 390, 391, 642
See application file for complete search history.

(56) References Cited

FOREIGN PATENT DOCUMENTS

| | | |
|---|---|---|
| KR | 101205510 | 11/2012 |
| KR | 101432115 | 8/2014 |
| WO | 2014007624 | 1/2014 |

\* cited by examiner

MICROSCOPIC APPARATUS FOR CREATING SUPER-RESOLUTION IMAGES OF AN ORGANISM OR BIOLOGICAL MATTER AND METHOD FOR CREATING SUPER-RESOLUTION IMAGES OF AN ORGANISM OR BIOLOGICAL MATTER USING THE SAME

CROSS-REFERENCE TO RELATED APPLICATION

This application claims priority from and the benefit of Korean Patent Application No. 10-2015-0053700, filed on Apr. 16, 2015, which is hereby incorporated by reference for all purposes as if fully set forth herein.

BACKGROUND

Exemplary embodiments relate to microscopic apparatus and method for creating super-resolution images of at least one of an organism and biological matter. More particularly, exemplary embodiments relate to a microscopic apparatus for creating super-resolution images of an organism or biological matter, and a method for creating super-resolution images of an organism or biological matter using the microscopic apparatus.

DISCUSSION OF THE BACKGROUND

Visible light, a form of electromagnetic waves within a certain wavelength range, scattered from an object enables an image creation of the object and a recognition of the shape of the object. The scattered light from the object has components of evanescent waves and propagating waves, and the properties of the evanescent waves and the propagating waves are opposite each other. Since most of the evanescent waves disappear within a distance of tens of nanometers from the surface of a material after being generated and are thus not able to create a recognizable image, recognizable images of an object are created by the propagating waves. Rapid attenuation of the evanescent waves causes the diffraction limit that limits resolving power of an optical system.

In an optical system for observing small objects, the resolving power is a measure representing the definition of shown images that are obtained through the optical system. For example, resolving power 'd' of the optical system indicates that it is possible to recognize that two objects are separated by using the optical system when the two objects are spaced apart from each other with a distance equal to or greater than 'd'.

In the theory of general optics, it has been generally accepted that the resolving power cannot be reduced more than ½ of the wavelength of light used for observing objects in an optical system using propagating waves for creating images thereof. Therefore, if an ordinary optical microscope is used for creating images of an object by illuminating the object with visible light, the resolving power of the ordinary optical microscope is limited to approximately 200 nm or smaller which is approximately a half wavelength of the purple light which is the shortest wavelength among visible light rays. Accordingly, an electron microscope, which uses electrons having a wavelength even shorter than visible light, has been utilized to observe viruses, single molecules, or smaller biological matters, for example, DNA or neurons.

However, electron microscopes have several limits to being used by general users, and are more expensive in comparison with optical microscopes. Furthermore, if targets of the electron microscope are organisms, electron beams may kill them, and it is essential to prepare a specimen to be observed as a solid matter to endure the vacuum condition of the electron microscope. Therefore, it is difficult to observe living organisms or biological matter by using electron microscopes.

In order to overcome such problems, methods of amplifying the evanescent waves or changing the evanescent waves to the propagating waves to create object images have been developed as a solution to overcome the resolving power limit. For example, a hyper-lens may change the evanescent waves to the propagating waves and magnify the size of images by using cylindrical anisotropic metamaterials. Because the propagating waves changed by the hyper-lens are attenuated less than the evanescent waves, the transformed propagating waves may create magnified long-range images formed far away from the rear side of the hyper-lens, and thus allow users to observe images of the object which is smaller than the resolving power of visible light. In this case, because the evanescent waves reflected from the object should reach the hyper-lens before disappearing, the object needs to be positioned close to the front side of the hyper-lens such that the distance therebetween is not longer than tens of nanometers.

The hyper-lens enables users to observe objects smaller than the resolving power of visible light when optical microscopic devices are used. However, conventional hyper-lenses are constructed to function in a wavelength range in the ultraviolet region of which the wavelength is smaller than 400 nm or the infrared region of which the wavelength is greater than 700 nm. Such optical microscopes still have problems for practical use.

The above information disclosed in this Background section is only for enhancement of understanding of the background of the inventive concept, and, therefore, it may contain information that does not form the prior art that is already known to a person of ordinary skill in the art.

SUMMARY

Exemplary embodiments relate to microscopic apparatus and method for creating super-resolution images of at least one of an organism and biological matter.

Additional aspects will be set forth in the detailed description which follows, and, in part, will be apparent from the disclosure, or may be learned by practice of the inventive concept.

An exemplary embodiment discloses an optical microscopic apparatus for creating a super-resolution image of an organism or biological matter, the optical microscopic apparatus including: a light source configured to provide visible light including evanescent waves; a hyper-lens unit including a front surface on which a specimen is placed, the hyper-lens unit including a multi-layered structure to convert at least part of the evanescent waves incident on the front surface into propagating waves; an objective lens for collecting visible light emitted from a rear surface of the hyper-lens unit; and an image capturing unit to capture visible light emitted from the objective lens and to create an image of the specimen.

An exemplary embodiment further discloses a method for creating a high-resolution image of an organism or biological matter, the method including: immersing a hyper-lens unit in a liquid medium for culturing a specimen on one side of the hyper-lens unit, the hyper-lens unit including a multi-layered structure to convert at least part of evanescent waves incident on the one side into propagating waves; creating visible light to illuminate the one side of the hyper-lens unit; collecting light leaving the other side of the hyper-lens unit; and obtaining the collected light to create an image of the specimen.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. As such, the regions illustrated in the drawings are schematic in nature and their shapes are not necessarily intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

Hereinafter, exemplary embodiments of the present invention will be described in detail with reference to the accompanying drawings.

In the following description, the front (front side) and the rear (rear side) may be specified to match the direction of travelling light illuminated by a light source unit. For example, when the light travels from a first configuration to a second configuration, the first configuration may be located in the front of the second configuration, and the second figuration may be located behind the first configuration. In addition, in one configuration, the side on which light is incident may be referred to as a front side, and the side from which light leaves may be referred to as a rear side.

Figure 1:
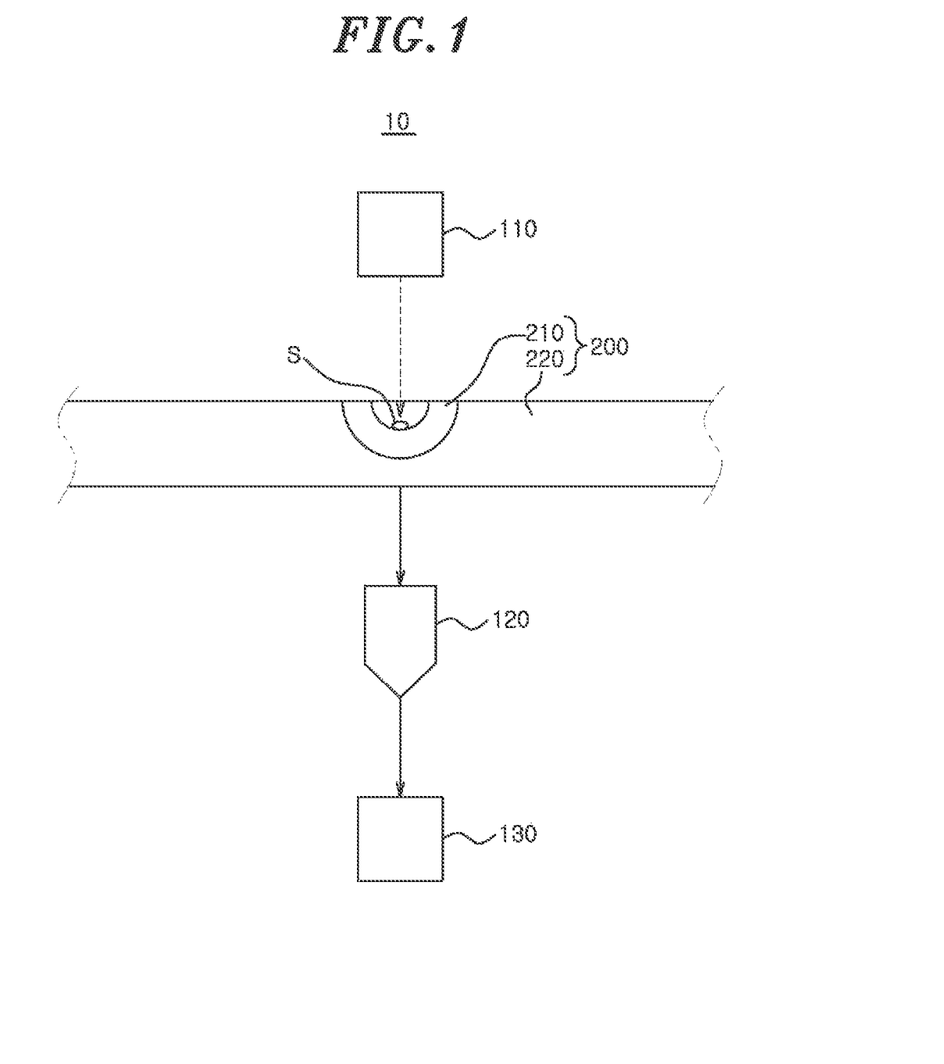
FIG. 1 shows a configuration of a microscopic apparatus for creating super-resolution images of an organism or biological matter in accordance with an exemplary embodiment.
Figure 2:
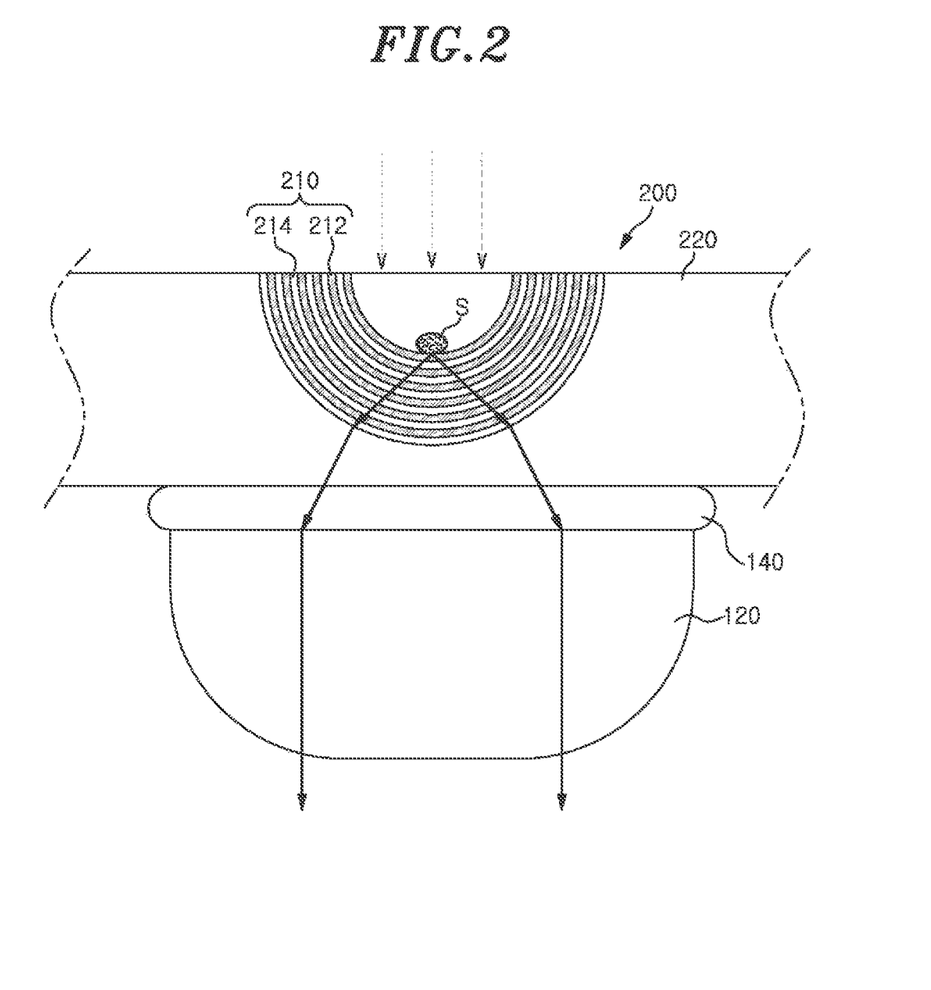
FIG. 2 is a schematic cross sectional view of a hyper-lens unit and an objective lens shown in FIG. 1.
Figure 3:
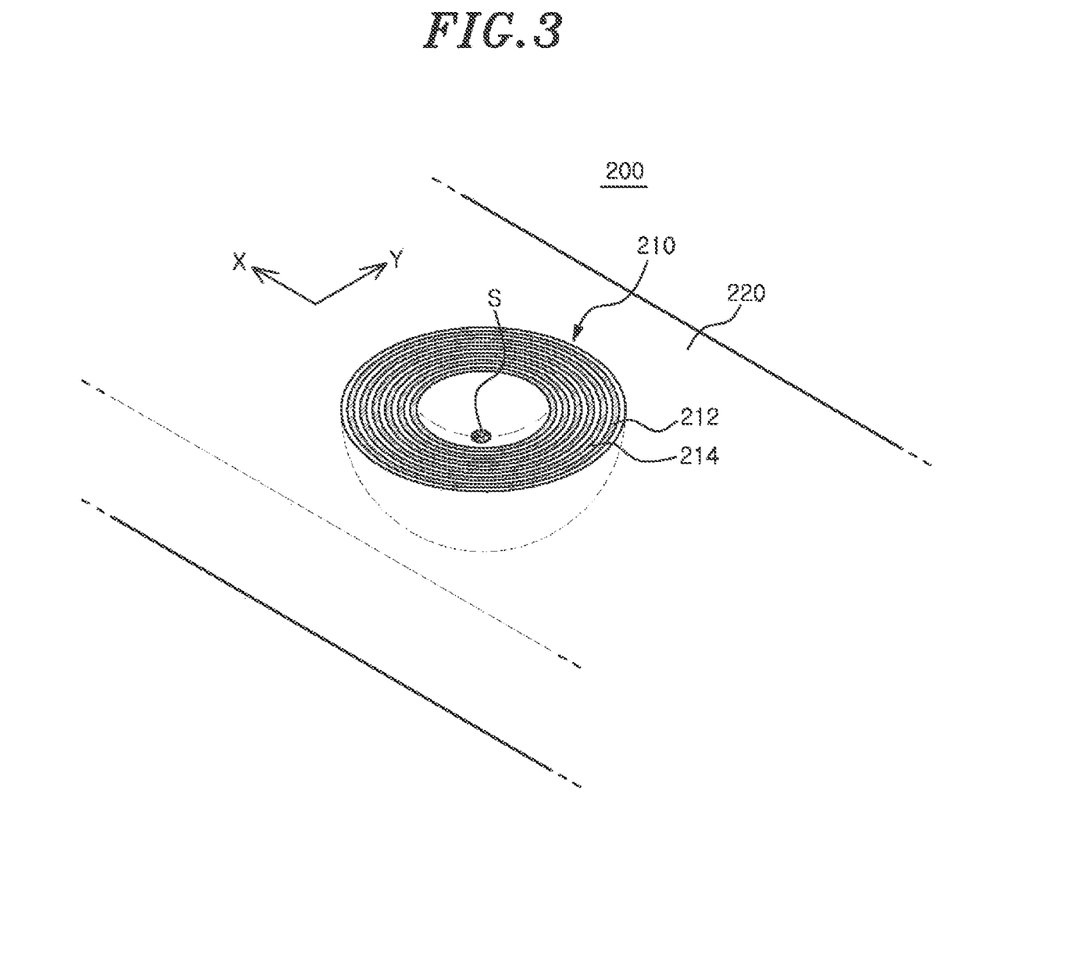
FIG. 3 is a perspective view of the hyper-lens unit shown in FIG. 2.

FIG. 1 is a configuration of a microscopic apparatus for creating super-resolution images of an organism or biological matter in accordance with an exemplary embodiment, and FIG. 2 is a schematic cross sectional view of a hyper-lens unit and an objective lens shown in FIG. 1. FIG. 3 is a perspective view of the hyper-lens unit shown in FIG. 2.

Referring to FIG. 1, FIG. 2, and FIG. 3, the microscopic for creating super-resolution images of an organism or biological matter S may include a light source unit 110, a hyper-lens unit 200, an objective lens 120, and an image capturing unit 130.

The light source unit 110 is configured to illuminate the hyper-lens unit 200 with light. The light source unit 110 may be configured to illuminate the hyper-lens unit 200 with light in a specific wavelength range. For example, the light source unit 110 may illuminate the hyper-lens unit 200 with visible light. More specifically, the wavelength of the light emitted from the light source unit 110 may be in a range from 400 nm to 700 nm. However, the light used in illumination by the light source unit 110 is not limited thereto, and, for example, the light source unit 110 may illuminate the hyper-lens unit 200 with ultraviolet rays in a wavelength range shorter than visible light, or infrared rays in a wavelength range longer than visible light.

In addition, the light used in illumination by the light source unit 110 may be light not artificially polarized. For example, the light source unit 110 may illuminate the hyper-lens unit 200 with visible light which is natural and not polarized in a wavelength range from 400 nm to 700 nm. Therefore, the microscopic apparatus 10 may be configured without adding an additional color filter for selecting a required optical spectrum or a polarizing filter for polarization, and thus, the structure of the microscopic apparatus 10 may be simplified.

The hyper-lens unit 200 may be provided in the rear side of the light source unit 110. The light leaving the light source unit 110 may be incident on the hyper-lens unit 200. The hyper-lens unit 200 may be a substrate on which a specimen observed by the microscopic apparatus 10 is placed. The hyper-lens unit 200 can change evanescent waves generated when the light is incident on the specimen into propagating waves and also magnify the specimen image to form a long-range image in a location relatively far away.

In this disclosure, the specimen means an object to be observed using the microscopic apparatus 10, and may be an organism or biological matter S smaller than the resolving power of visible light (sub diffraction limit). For example, the specimen may be any one of neurons, DNA, bacteria, viruses, single molecular cells and lipids, but exemplary specimens are not limited thereto.

Specifically, the hyper-lens unit 200 may include a lens layer 210 on which the specimen may be placed, and a substrate layer 220 for supporting the lens layer 210.

The lens layer 210 may be configured to include a hyper-lens, and the central part of the front side of the hyper-lens is concave. The hyper-lens is a lens to form images of the specimen by using evanescent waves of the light used in illumination and scattering on the specimen to be observed. The lens layer 210 may have a ring-shaped section centered on the concave part, and may be an anisotropic metamaterial with a structure layered alternately with a plurality of dielectric layers 212 and a plurality of metallic layers 214.

In accordance with an exemplary embodiment, the lens layer 210 may be an anisotropic metamaterial for light in a wavelength range from 400 nm to 700 nm. Therefore, when evanescent waves scattering and generated from visible light are incident on the lens layer 210, they may change into propagating waves without being attenuated.

For example, the dielectric layer 212 may include or may be made of titanium oxide $Ti_3O_5$, and the metallic layer 214 may include or may be made of silver Ag. The dielectric layer 212 and the metallic layer 214 may be as thick as 30 nm, respectively, and the same number of the dielectric layers 212 and the metallic layers 214 may be layered alternately each other. For example, nine dielectric layers 212 and nine metallic layers 214 may be layered alternately to form the lens layer 210. In this case, longer wavelengths of the visible light incident on the hyper-lens unit 200 from the light source unit 110 may be preferably 400 nm to 500 nm. Preferably, visible light rays having wavelength of 410 nm may be used in illumination by the light source unit 110.

In another example, the dielectric layer 212 may include or may be made of silicon Si, and the metallic layer 214 may include or may be made of silver Ag. In this case, the silicon dielectric layer 212 may be made of non-crystalline or amorphous silicon formed through sputtering. Each of the dielectric layer 212 and the metallic layer 214 may be as thick as 15 nm, respectively, and the nine dielectric layers 212 and the nine metallic layers 214 may be layered alternately to form the lens layer 210. However, the total number of the dielectric layers 212 and the metallic layers 214 are not limited as such. If the lens layer 210 is formed in accordance with this example, visible light with a wavelength in a range from 500 nm to 650 nm may be used in illumination by the light source unit 110.

The specimen may be placed on the concave central part of the lens layer 210. In this case, the specimen may be positioned to closely contact the outermost layer of the lens layer 210 as shown in e.g., FIG. 2. Therefore, the lens layer 210 and the specimen may be positioned at a distance of a fraction of the wavelength of the light leaving the light source unit 110. The evanescent waves of the light scattering and used in illuminating the specimen are incident on the lens layer 210, amplified and radially magnified while passing through the lens layer 210. Components of evanescent waves changed into propagating waves while passing through the lens layer 210 may pass through the substrate layer 220, and then travel through the air to form a magnified specimen image at a specific location distanced away from the rear side of the lens layer 210.

As shown in FIG. 3, the lens layer 210 may be shaped like a hemisphere by layering the dielectric layers 212 and the metallic layers 214. In this case, when non-polarized light is incident on the hyper-lens unit 200 from the light source unit 110 and used in illumination, a two-dimensional long-range image may be formed. More specifically, the lens layer 210 may amplify and magnify components of the evanescent waves in the y direction and in the x direction. Therefore, two-dimensional long-range images reflecting the two-dimensional shape of the specimen may be formed in the rear side of the lens layer 210. In addition, if the specimen is placed on the concave part of the hemispherical lens layer 210, the specimen may be moved to the central part by the hemispherical shape of the lens layer 210 and the gravitational force. Consequently, the specimen may be effectively secured in the optimal position while closely contacting the outermost layer of the lens layer 210 in the concave space of the lens layer 210.

The substrate layer 220 may support the lens layer 210, and allow the light to pass through the lens layer 210. For example, the substrate layer 220 may include or may be made of quartz.

The objective lens 120 may be provided in the rear side of the hyper-lens unit 200. The objective lens 120 may be implemented such that the light emitted from the light source unit 110 and passing through the hyper-lens unit 200 is incident on the image capturing unit 130. To this end, the objective lens 120 may face the rear side of the hyper-lens unit 200. In an example, immersion oil 140 may be provided between the objective lens 120 and the hyper-lens unit 200, and the objective lens 120 may be positioned to contact the immersion oil 140. The immersion oil 140 may be applied to implement the refractive index of the objective lens 120 and the hyper-lens unit 200 to match each other. In addition, the objective lens 120 may have a numerical aperture of ×100.

The image capturing unit 130 may be provided in the rear side of the objective lens 120 to create a specimen image with the light emitted from the objective lens 120. More specifically, the image capturing unit 130 may receive a magnified long-range image of the specimen formed by the hyper-lens unit 200 through the objective lens 120, and convert the specimen image to an image based on the specimen image and output the converted image. The image capturing unit 130 may be an imaging apparatus, for example, a camera. Specifically, the image capturing unit 130 may be a CCD (Charge-Coupled Device) camera module, which has an array of light collectors in a closed space, and allows the energy patterns of photons of incident light to be converted to discrete analog signals. Through this process, the CCD camera module may create a specimen image.

As described above, the specimen may be an organism or biological matter S smaller than the size normally viewable with the resolving power of visible light (hereinafter, sub-diffraction limit size). In this case, the organism or biological matter S may be living organisms. Furthermore, the organism or biological matter S may be placed directly on the front surface of the lens layer 210 of the hyper-lens unit 200.

Conventionally, an electron microscope has been used to observe the nano-structure of an organism or biological matter, and optical microscopes could not be used to view objects smaller than the size viewable with the resolving power of the optical microscopes. However, since the electron microscope uses a vacuum chamber and electron beams which kill live an organism or biological matter, it may be difficult to observe an organism or biological matter while they are alive. In addition, although it is possible to observe an organism or biological matter while they are alive by using a conventional microscope, for example, STROM or PALM, these microscopic apparatuses have to obtain thousands to tens of thousands of still images to provide an image edited with the still images. Therefore, it may be difficult to observe the movement of living organisms in real time. According to an exemplary embodiment, since a vacuum chamber is not required, and the organism or biological matter S are illuminated with visible light of which the energy is smaller than the energy of ultraviolet rays, the organism or biological matter S may be observed while they are alive and active in real time. In addition, the specimen image may be obtained in real time and may be captured as video image data. As a result, the images of moving an organism or biological matter S may be observed more efficiently.

For example, the stem of neurons is as thick as approximately 150 nm, and the space between synapses ranges from approximately 30 nm to 50 nm. Since the microscopic apparatus 10 has a greater resolving power than that of a conventional optical microscope and capable of discerning the neuron structure, it is possible to observe a synapse structure of the neurons. Furthermore, since the neurons may be observed while they are alive, it is possible to obtain images of the neurotransmitters transmitted through the synapses. In addition, an organism or biological matter, for example, bacteria of 500 nm to 5 μm, viruses of 20 to 400 nm, red blood cells of approximately 10 μm, ribosomes or micelles may be observed in real time while they are alive. The microscopic apparatus 10 may provide an enlarged image of a specimen having a size of about 20 nm to about 35 nm, which is about one twentieth of wavelengths of visible light.

Consequently, the microscopic apparatus 10 enables users to create super-resolution images of an organism or biological matter S of which the size is not greater than a sub diffraction limit, and they may be observed while they are alive. Accordingly, it allows users to create super-resolution images of the nano-structure and movement of an organism or biological matter S of which the size is not greater than the sub diffraction limit in real time. Further, while enabling observations of live micro organisms, it allows users to obtain the super-resolution images in real time by using the microscopic apparatus 10 relatively economically constructed in comparison with electron microscopes. In particular, using the microscopic apparatus 10 is more user-friendly and convenient since an organism or biological matter S of which the size is not greater than the sub diffraction limit are observed by using natural visible light not polarized or filtered.

Figure 4:
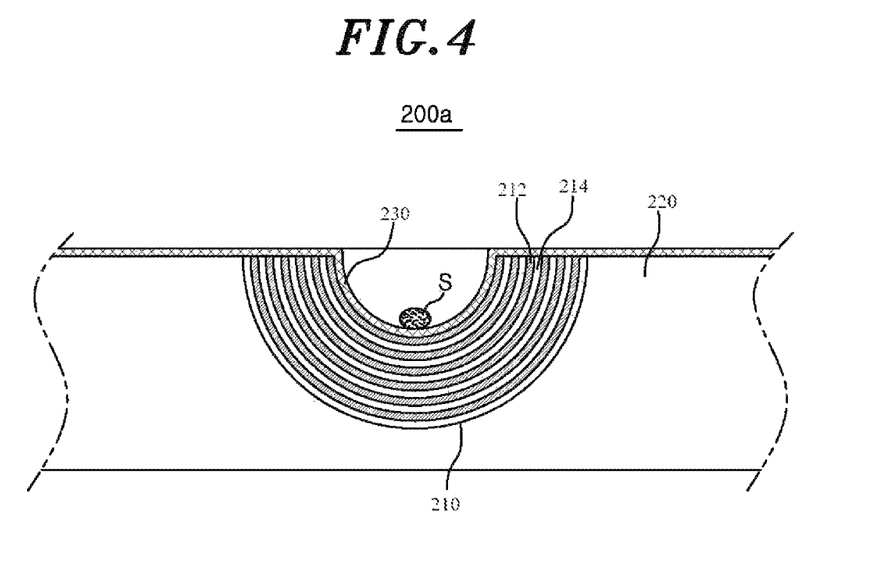
FIG. 4 is a cross-sectional view of a hyper-lens unit of a microscopic apparatus for creating super-resolution images of an organism or biological matter in accordance with an exemplary embodiment.
Figure 5:
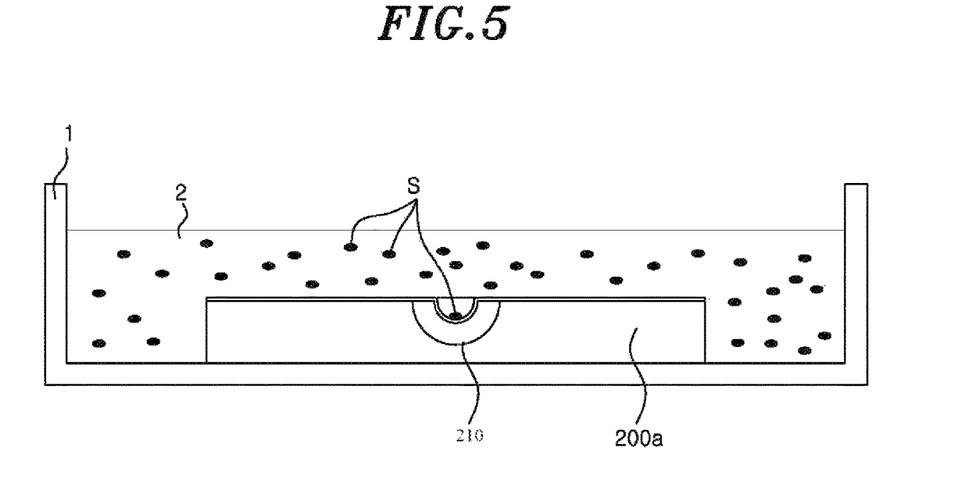
FIG. 5 is a diagram illustrating a placement of a specimen on the hyper-lens unit shown in FIG. 4 in accordance with an exemplary embodiment.

FIG. 4 is a cross-sectional view of a hyper-lens unit of a microscopic apparatus for creating super-resolution images of an organism or biological matter in accordance with an exemplary embodiment, and FIG. 5 is a diagram illustrating a placement of a specimen on the hyper-lens unit shown in FIG. 4 in accordance with an exemplary embodiment.

Referring to FIG. 4, the hyper-lens unit 200 of FIGS. 1 and 2 may be modified to the hyper-lens unit 200a of FIG. 4, which further includes a protection film 230.

The protection film 230 may be layered on the outer side of the lens layer 210 and the substrate layer 220 to cover the lens layer 210 of the hyper-lens unit 200a. For example, as shown in FIG. 4, the protection film 230 may cover both the outermost layer of the lens layer 210 and the outer surface on the side of substrate layer 220 where the lens layer 210 is provided. In this case, the protection film 230 may closely contact the concave central part of the lens layer 210. The protection film 230 may be a precautionary measure to prevent the lens layer 210 from being damaged when the organism or biological matter S to be observed in the microscopic apparatus 10 directly contact the lens layer 210.

Specifically, the protection film 230 may be made of a material for preventing liquid permeation. For example, the protection film 230 may be a glass layer. In this case, the glass layer may be formed by carrying out atomic layer deposition on the front surface of the lens layer 210, and as thick as approximately 3 nm.

Referring to FIG. 5, the organism or biological matter S to be observed in the microscopic apparatus 10 may be cultured directly on the hyper-lens unit 200*a*. More specifically, the specimen placed on the concave part of the lens layer 210 may be a specimen grown directly on the hyper-lens unit 200*a*.

To this end, the hyper-lens unit 200*a* may be put in a container 1 filled with liquid medium 2 for growing the specimen. While the hyper-lens unit 200*a* is immersed in the liquid medium 2, the organism or biological matter S to be observed may be cultured at required temperature and humidity levels. Since the hyper-lens unit 200*a* is immersed in the liquid medium 2, the number of an organism or biological matter S may increase and some of them may gather in the concave part of the lens layer 210 as culture progresses. In this case, an attraction force similar to the principle of capillary action occurs in the concave part of the lens layer 210. By the force, the organism or biological matter may grow while they closely contact the surface of the concave part of the lens layer 210.

If the hyper-lens unit 200*a* is placed in the liquid medium to grow the organism or biological matter directly on the hyper-lens unit 200*a* as described above, the liquid medium may permeate into the lens layer, and it may damage the hyper-lens unit 200*a* without the protection film 230. If the lens layer have a layered structure as described above, the liquid medium may penetrate into the lens layer through defects that may occur while depositing the metallic layer 214 on the nonmetallic layer 212. Accordingly, interlayer separation may occur by means of capillary action in locations of weak adhesion. However, since the protection film 230 for preventing liquid permeation is formed on the outer side of the lens layer 210, the protection film 230 prevents the liquid medium 2 from permeating into the lens layer 210. Therefore, although the hyper-lens unit 200*a* is immersed in the liquid medium 2, the lens layer 210 is not damaged by the liquid medium 2, and culturing the organism or biological matter S to be observed directly on the hyper-lens unit 200*a* is thus enabled without damaging the lens layer 210.

Growing the organism or biological matter S directly on the hyper-lens unit 200*a* enhances the integration of the process of culturing the organism or biological matter S elsewhere with the process of placing the whole an organism or biological matter S on the lens layer 210. In addition, this integrated process also reduces the chance of killing or damaging the organism or biological matter S while locating them on the lens layer 210. Furthermore, since the living organism or biological matter S is generally more active in the concave part of the lens layer 210, it is even easier to observe the movement of the organism or biological matter S using the concave structure.

Figure 6:
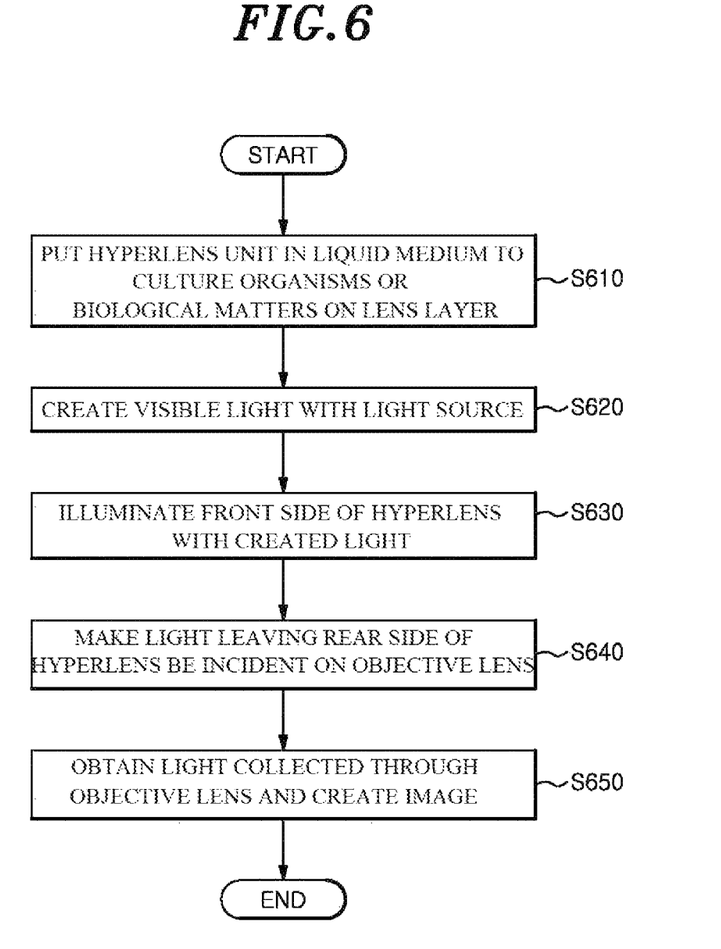
FIG. 6 is a flowchart illustrating a method for creating super-resolution images of an organism or biological matter in accordance with an exemplary embodiment.

Hereinafter, a method for creating a super-resolution image using the microscopic apparatus 10 explained above will be described in more detail. FIG. 6 is a flowchart illustrating a method for creating super-resolution images of an organism or biological matter in accordance with an exemplary embodiment.

First, a specimen may be placed on the hyper-lens unit 200 as shown in FIG. 2 or the hyper-lens unit 200*a* as shown in FIG. 4. For example, the specimen may be an organism or biological matter S of which the size is not greater than a sub diffraction limit, and the organism or biological matter S may be cultured while the hyper-lens unit 200 is immersed in the liquid medium 2 for the organism or biological matter S in operation S610. The organism or biological matter S may be living organisms.

The light source unit 110 may emit light including visible light rays in operation S620. The light may include visible light rays in a specific wavelength range, or visible light rays within the entire visible light wavelength range. In the latter case, the light emitted by the light source unit 110 may be natural light not filtered through a special filter, e.g., a color filter, or a polarizer.

The light emitted by the light source unit 110 may illuminate the front side of the hyper-lens unit 200 or 200*a* while the organism or biological matter S are placed on the lens layer 210 in operation S630. In this case, the organism or biological matter S placed on the lens layer 210 may remain alive.

The illuminating light may generate evanescent waves including information about the nano-structure of the organism or biological matter S. The generated evanescent waves may be amplified by the lens layer 210 to be changed into propagating waves, and pass through the lens layer 210 while being extended two-dimensionally. The light passing through the lens layer 210 may pass through the substrate layer 220 and leave the rear side of the hyper-lens unit 200 or 200*a*.

The light leaving the rear side of the hyper-lens unit 200 or 200*a* may be incident on the objective lens 120 in operation S640. In this case, it is possible to further enhance the resolving power by controlling various magnifications. In addition, for effective collection of light, the end of the objective lens 120 may contact the immersion oil 140.

The light collected by the objective lens 120 may be incident on the image capturing unit 130 which may create the image of organisms or biological matters S of which the size is not greater than the sub diffraction limit on the basis of the incident light in operation S650. Specifically, the image capturing unit 130 may be a charge-coupled device (CCD) camera. The CCD camera module may convert photon energy patterns of light incident through a light collector array in a closed space to discrete analog signals to create images of the living an organism or biological matter S in real time.

In view of the above, one or more exemplary embodiments disclose an optical microscope having a hyper-lens. Therefore, one or more exemplary embodiments provides a practical microscopic apparatus for conveniently and effectively observing an organism or biological matter smaller than the resolving power of visible light of conventional optical microscopes, and a method for creating super-resolution images of an organism or biological matter by using the microscope apparatus.

As set forth above, a microscopic apparatus for creating super-resolution images of an organism or biological matter and a method for creating super-resolution images of an organism or biological matter by using the microscopic apparatus exhibit at least one of the following effects.

A hyper-lens allows users to observe an organism or biological matter smaller than the resolving power of visible light by using the evanescent waves of visible light. Since organisms or biological matters are not killed by visible light, this allows users to observe them in real time while they are alive.

According to one or more exemplary embodiment, users may be enabled to observe an organism or biological matter through an optical microscopic apparatus using non-polarized visible light, and the super-resolution microscopic apparatus may have simpler configuration and improved usability.

Exemplary embodiments of a microscope apparatus and a method for creating super-resolution images of an organism or biological matter are described above. It should be noted, however, that they are only examples, and the present invention is not limited thereto, but should be understood to have the broadest range in compliance with the basic idea disclosed in this specification. Although those skilled in the art may combine/replace the disclosed embodiments to devise patterns in shapes not described, it should be noted that they are also within the range of the present invention.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. An optical microscopic apparatus for creating a super-resolution image of an organism or biological matter, the optical microscopic apparatus comprising:
    a light source configured to provide visible light comprising evanescent waves;
    a hyper-lens unit comprising a front surface on which a specimen is placed, the hyper-lens unit comprising a multi-layered structure to convert at least part of the evanescent waves incident on the front surface into propagating waves;
    an objective lens for collecting visible light emitted from a rear surface of the hyper-lens unit; and
    an image capturing unit to capture visible light emitted from the objective lens and to create an image of the specimen,
    wherein the hyper-lens unit is detachable, and
    wherein the specimen is cultured on the front surface of the hyper-lens unit while the hyper-lens unit is immersed in a liquid medium for the specimen.

2. The optical microscopic apparatus of claim 1, wherein the specimen comprises a live organism having a size smaller than one half of a shortest wavelength of the visible light, and
    wherein the hyper-lens unit is configured to enlarge an image of the live organism, the image of the live organism when created by the image capturing unit being discernible by a human eye.

3. The optical microscopic apparatus of claim 1, wherein the specimen comprises a neuron having a size about 150 nm, and
    wherein the hyper-lens unit is configured to enlarge an image of the neuron, the image of the neuron when created by the image capturing unit being discernible by a human eye.

4. The optical microscopic apparatus of claim 1, wherein the specimen comprises at least one organism having a size smaller than one half of a shortest wavelength of the visible light, and
    wherein the organism is any one of a deoxyribonucleic acid (DNA), a bacteria, a virus, single molecular cell, and a lipid.

5. The optical microscopic apparatus of claim 1, wherein the hyper-lens unit comprises:
    a lens layer having the front surface on which the specimen is placed, the front surface having a concave portion; and
    a substrate layer for supporting the lens layer and covering a back side of the lens layer.

6. The optical microscopic apparatus of claim 5, wherein the lens layer has a hemisphere shape by alternately layering a plurality of dielectric layers and a plurality of metallic layers.

7. The optical microscopic apparatus of claim 6, wherein the dielectric layers comprise titanium oxide $Ti_3O_5$, and the metallic layers comprise silver Ag, and wherein the visible light has wavelengths within a range of 400 nm to 500 nm.

8. The optical microscopic apparatus of claim 6, wherein the dielectric layers comprise silicon Si, and the metallic layers comprise silver Ag.

9. The optical microscopic apparatus of claim 8, wherein the dielectric layers comprise non-crystalline or amorphous silicon formed through sputtering.

10. The optical microscopic apparatus of claim 9, wherein each of the dielectric layers and each of the metallic layers have thicknesses less than or equal to 15 nm, respectively.

11. The optical microscopic apparatus of claim 8, wherein the visible light has wavelengths within a range of 500 nm to 650 nm.

12. The optical microscopic apparatus of claim 1, wherein the hyper-lens unit further comprises a protection film covering the lens layer, the protection film comprising a material for preventing liquid permeation, and wherein the specimen is configured to be disposed on the protection film.

13. The optical microscopic apparatus of claim 12, wherein the protection film comprises a glass layer.

14. The optical microscopic apparatus of claim 13, wherein the protection film is deposited on the lens layer by an atomic layer deposition.

15. The optical microscopic apparatus of claim 2, wherein the image capturing unit creates video image data including real time movements of the specimen.

16. The optical microscopic apparatus of claim 1, wherein the visible light incident on the hyper-lens unit is non-polarized visible light.

17. The optical microscopic apparatus of claim 1, further comprising:
    immersion oil provided between the objective lens and the hyper-lens unit.

18. A method for creating a high-resolution image of an organism or biological matter, the method comprising:
    immersing a hyper-lens unit in a liquid medium for culturing a specimen on one side of the hyper-lens unit, the hyper-lens unit comprising a multi-layered structure to convert at least part of evanescent waves incident on the one side into propagating waves;
    creating visible light to illuminate the one side of the hyper-lens unit;
    collecting light leaving the other side of the hyper-lens unit; and
    obtaining the collected light to create an image of the specimen.

19. The method of claim 18,
    wherein the specimen comprises a live organism having a size smaller than one half of a shortest wavelength of the visible light, and
    wherein the hyper-lens unit is configured to enlarge an image of the live organism, the image of the live organism when created by an image capturing unit being discernible by a human eye.

* * * * *